United States Patent [19]

Frommer et al.

[11] Patent Number: 5,750,362
[45] Date of Patent: May 12, 1998

[54] METHODS FOR IDENTIFYING SUBSTANCES WITH A POTENTIAL HERBICIDAL OR GROWTH-REGULATING ACTION BY MEANS OF PLANT TRANSPORTER PROTEINS, THE USE OF THE TRANSPORTER PROTEINS, AND SUBSTANCES WITH A HERBICIDAL AND GROWTH-REGULATING ACTION

[75] Inventors: Wolf-Bernd Frommer; Olaf Ninnemann; Wolfgang Streber; Jörg Riesmeier; Marion Kwart, all of Berlin, Germany

[73] Assignee: BASF Aktiengesellschaft, Ludwigshafen, Germany

[21] Appl. No.: 663,222

[22] PCT Filed: Dec. 15, 1994

[86] PCT No.: PCT/EP94/04174

§ 371 Date: Aug. 5, 1996

§ 102(e) Date: Aug. 5, 1996

[87] PCT Pub. No.: WO95/16913

PCT Pub. Date: Jun. 22, 1995

[30] Foreign Application Priority Data

Dec. 16, 1993 [DE] Germany ............ 43 43 527.0

[51] Int. Cl.$^6$ .................................. G12Q 1/02
[52] U.S. Cl. .................. 435/29; 435/69.1; 435/71.1; 435/171; 435/172.3; 435/254.11
[58] Field of Search .................. 435/71.1, 69.1, 435/254.2, 29, 171, 172.3, 254.11

[56] References Cited

FOREIGN PATENT DOCUMENTS 43 37 597  10/1993  Germany .
90/06047   6/1990   WIPO .
94/00574   1/1994   WIPO .
94/01559   1/1994   WIPO .

OTHER PUBLICATIONS

Giaquinta, *Nature*, 267: 369–370, 1977.
*Plant Physiol.*, 34: 347–387, 1983.
Delrot & Bonnemain, *Plant Physiol.*, 67: 560–564, 1981.
Bush, *Plant Physiol.*, 89: 1218–1323, 1989.
Reismeier et al., *Plant Cell*, 5: 1591–1598, 1993.
Reismeier et al., *Embo J.*, 11: 4705–4713, 1992.
Sauer & Tanner, *Plant Physiol.*, 79:760–764, 1985.
Reins et al., *Plant Physiol.*, 97:227–233, 1991.
Schobert & Komor, *Planta*, 177: 342–349, 1989.
*Planta*, 181: 85–90, 1990.
Li & Bush, *Plant Physiol.*, 94: 268–277, 1991.
Kwart et al., *Planta J.*, 4: 993–1002, 1993.
Ljingdahl et al., *Cell*, 71: 463–478, 1992.
Ninnemann et al., *Embo J.*, 13: 3464–3471, 1994.
Hediger et al., *Nature*, 330: 379–381, 1987.
Sauer et al., *Embo J.* 9: 3045–3050, 1990.
Flügge et al., *Embo J.*, 8: 39–46, 1989.
Willmitzer, *Trends Genet*, 4: 13–18, 1988.
Reismeier et al., *Proc. Natl. Acad. Sci.*, 90: 6160–6164, 1993.
Reismeier et al., *Embo J.*, 13: 1–7, 1994.
Jauniaux & Grenson, *Eur. J. Biochem.*, 190: 39–44, 1990.
Tanaka & Fink, *Gene*, 38: 205–214, 1985.

*Primary Examiner*—James Ketter
*Assistant Examiner*—Irem Yucel
*Attorney, Agent, or Firm*—Keil & Weinkauf

[57] ABSTRACT

A method for identifying substances with a potential herbicidal and growth-regulating action by means of plant transporter proteins (transporters), the use thereof and substances identifiable by the method and having a herbicidal and growth-regulating action are described.

9 Claims, No Drawings

METHODS FOR IDENTIFYING SUBSTANCES WITH A POTENTIAL HERBICIDAL OR GROWTH-REGULATING ACTION BY MEANS OF PLANT TRANSPORTER PROTEINS, THE USE OF THE TRANSPORTER PROTEINS, AND SUBSTANCES WITH A HERBICIDAL AND GROWTH-REGULATING ACTION

The present invention relates to methods for identifying substances with a potential herbicidal or growth-regulating action by means of plant transporter proteins (transporters), to the use thereof, and to substances identifiable by the method and having a herbicidal or growth-regulating action.

Novel crop protection agents are required to have lower toxicity, greater environmental compatibility and improved efficacy by comparison with conventional agents. is The probability of successfully finding such substances depends, besides the number of substances available, essentially on the method used to identify the active substances. Since conventional methods are usually based on direct testing of substances for their herbicidal or growth-regulating activity on plants, these methods are, a rule, very time-consuming and costly and require extensive trial areas. Consequently, comparatively few substances can be tested at the same time.

There is therefore a need for methods which can be carried out simply and rapidly in order to permit a sufficient number of substances to be investigated.

We have now found a method which can be used to identify chemical compounds which specifically interact with a transporter protein from plants. The method comprises, according to the invention, initially testing these substances on a transgenic organism, preferably a unicellular organism, which functionally expresses a plant transporter protein, or on transgenic cells which functionally express a plant transporter protein, for inhibition of the transport process.

The substances identified thereby as inhibitory are subsequently investigated for their effect on whole plants. The term transporter proteins means for the purposes of this invention proteins which are responsible for transporting substances through membranes in plant cells. In the method according to the invention, a plant transporter protein is integrated into a test system which makes it possible to determine, qualitatively and quantitatively, with biochemical, microbiological and physiological methods of measurement, the membrane transport function. The use of this test system makes it possible specifically to find active substances which are able to interact with the transport proteins of the plant. Interaction of substances with a transporter protein may bring about inhibition or inactivation of the transport process and, moreover, may lead to transport of the substance itself. Since transport processes play a central part in overall plant metabolism and are often essential for growth of plants, the method according to the invention makes it possible to identify, specifically and with higher probability, substances which exert an effect on plant growth. The interaction may elicit a growth-regulating or herbicidal action if the substance which is found leads to inhibition of the natural transport process. In the event that the substance with inhibitory activity is itself transported, it may, as ingredient of crop protection agents, such as fungicides, insecticides, nematicides and acaricides, especially herbicides and growth regulators, increase their mobility in plants and thus lead to novel agents which are more effective. The test system according to the invention can furthermore be used to investigate plant transporter proteins at the molecular level.

To date no methods have been described for identifying substances with a herbicidal or growth-regulating action by means of a plant transporter protein. There has likewise been no description of the inhibition of plant transport processes as mechanism of action of herbicides. Furthermore, it is also unknown whether plant transporter proteins represent, because of their position in the metabolism, eg. in supplying the organs of reproduction, an interesting potential target for herbicides or growth regulators.

The method according to the invention comprises a biochemical test system which, in its first stage, is preferably carried out on unicellular organisms or on cells maintained in cell culture. This test system has the advantage that, by comparison with conventional methods for identifying herbicidal or growth-regulating substances, it can be carried out rapidly and straight-forwardly. It further makes it possible to investigate, with little expenditure of time, a large number of substances for their herbicidal or growth-regulating action. The method according to the invention furthermore provides the advantage that it can be used specifically to identify those substances which interact with a very particular plant protein. In order to avoid unwanted effects on humans, animals and the environment, the target protein in the method can be chosen so that its function is specific for plants.

The proteins preferably employed as target proteins in the method according to the invention are those responsible in plants for transporting substances through membranes (transporter proteins), preferably those transporter proteins which are specific for plants.

The present invention thus relates to a method for identifying substances which have a potential herbicidal or growth-regulating action which arises due to inhibition or inactivation of a plant transport process, which comprises testing a chemical compound on a plant transporter protein for inhibition of the transport process, and then testing the compound which is active therein for its herbicidal or growth-regulating activity on plants, or comprises a) initially preparing the transporter protein by heterologous expression of a DNA sequence which codes for this transport protein in a transgenic organism or transgenic cells, subsequently b) employing this recombinant organism in its entirety or the transgenic cells for investigating a chemical compound for its inhibitory effect on said transporter protein, and c) additionally investigating the compound for activity on the organism or cell which does not produce the corresponding transporter, in order to preclude the possibility that the compound also has an inhibitory effect on other mechanisms in this organism or in the cell, and finally d) testing the compound which is active against the transporter for its herbicidal or growth-regulating activity on plants.

It is possible in general to use in the method according to the invention all transporter proteins which occur in plants, and the DNA sequences which code for the transporter proteins.

Various transporter proteins responsible for transporting substances through membranes have already been identified in plants, and in some cases DNA sequences which code for such transporter proteins are available.

Thus, for example, it has been possible to detect sucrose transporters directly on intact plants or on isolated leaf tissue. The sucrose uptake is in this case pH-dependent (Giaquinta, Nature 267: 369–370, 1977, Annu. Rev. Plant Physiol. 34: 347–387, 1983; Delrot & Bonnemain, Plant Physiol. 67: 560–564, 1981; Delrot, Plant Physiol. 67: 560–564, 1981). p-Chloromercuribenzyl-sulfonic acid and diethyl pyrocarbonate are highly effective transport inhibitors in this connection (Bush, 1989, Plant Physiol. 89: 1318–1323). cDNA sequences which code for plant sucrose transporters have already been described, for example for potatoes (p 62 and StSUT1) and spinach (S21 and SoSUT1) (WO 94/00574; Riesmeier et al., 1993, Plant Cell 5:1591–1598; Riesmeier et al., 1992, EMBO J. 11: 4705–4713), for *Arabidopsis thaliana* (suc1 and suc2 genes; EMBL gene bank: Access No. X75365), *Plantago major* (EMBL gene bank: Access No. X75764), *L. esculentum* (EMBL gene bank: Access No. X82275) and *Nicotiana tabacum* (EMBL gene bank: Access Nos. X82276 and X82277). In the case of the sucrose transporters, it was possible to clone cDNA sequences coding for these transporters from spinach and potato by developing an artificial complementation system in *Saccharomyces cerevisiae* (Riesmeier et al., EMBO J. 11: 4705–4713, 1992; Riesmeier et al., 1993, Plant Cell 5: 1591–1598).

Amino-acid transporters have likewise been identified in plants. The green alga Chlorella which is related to higher plants, has at least three different regulated amino-acid transport systems (Sauer and Tanner, Plant Physiol. 79: 760–764, 1985). This comprises active transport provided with energy from a proton gradient generated by H⊕-ATPase. In higher plants it has been concluded indirectly from investigation of the composition of xylem and phloem that a passive transport (facilitated diffusion) exists (Riens et al., Plant Physiol. 97: 227–233, 1991). In contrast to this, the phloem or xylem of ricinus cotyledons or roots, respectively, is loaded with amino acids selectively and counter to a concentration gradient (Schobert and Komor, Planta 177: 342–349, 1989; Planta 181: 85–90, 1990). It has been possible to demonstrate the existence of at least four independent H⊕ cotransporters in isolated vesicles in various plant species (Li and Bush, Plant Physiol. 94: 268–277, 1991). It was possible by comple-mentation of an amino-acid transport mutant of yeast to isolate and characterize ureide and amino-acid permease genes from *Arabidopsis thaliana*, for example cDNA sequences which code for the amino-acid transporters AAP1 and AAP2 (Frommer et al., 1993, Proc. Natl. Acad. Sci. USA 90:5944–5948; Kwart et al., 1993, Planta J. 4:993–1002; WO 94/01559). It was possible, with the aid of a complementation method using the yeast mutant shr3, which is no longer able to direct endogenous amino-acid transporters to the cell membrane (Ljungdahl et al., 1992, Cell 71: 463–478), to isolate a number of other DNA sequences which code for amino-acid transporters from plants, eg. cDNA sequences which code for the amino-acid transporters AAP3 (EMBL gene bank, Access Number: X77499), AAP4 (EMBL gene bank, Access Number: X77500), AAP5 (EMBL gene bank, Access Number: X77501), AAT1 (EMBL gene bank, Access Number: X71787) and NTR1 (EMBL gene bank, Access Number: X77503) from *Arabidopsis thaliana*. Also known are cDNA sequences which code for plant ammonium transporters, for example a cDNA coding for the ammonium transporter AMT1 from *Arabidopsis thaliana* (Ninnemann et al., 1994, EMBO J. 13:3464–3471; German Patent Application P 43 37 597.9; EMBL gene bank, Access Number: X75879).

The cloning of genes for membrane-bound transport proteins has already been described several times, besides the abovementioned examples. It is possible in principle for several different routes to be followed for cloning the genes of membrane proteins. For example, in the isolation of the glucose transporter gene from erythrocytes, it was possible to identify cDNA clones after purification of the protein (Mueckler et al., Science 229: 941–945, 1985). However, in many cases, it is so difficult to purify membrane transporters that other methods have to be used, eg. heterologous expression in oocytes (Hediger et al., Nature 330: 379–381, 1987). Plant plasmalemma H⊕-ATPase genes have been cloned via homology with animal and fungal genes. It has been possible to isolate plant glucose transporter genes from Chlorella by differential cDNA screening (Sauer et al., EMBO J. 8: 3045–3050, 1990). A cDNA clone from Chlorella has been used as heterologous probe for the cloning of several glucose transporter genes from higher plants (Sauer et al., 1990). The chloroplastidic triose phosphate translocator (TPT) was radiolabeled via the inhibitor DIDS, and the labeled protein was purified and partially sequenced. Synthetic oligonucleotides derived from the partial peptide sequences were used as probes for isolating TPT-encoding cDNAs (Flügge et al., EMBO J. 8: 39–46, 1989). The DNA sequences already known to code for plant transporter proteins can in turn be used to identify and isolate other DNA sequences which code for transporter proteins from plants by means of conventional techniques of molecular biology.

Genes preferably used in the method according to the invention code for transporter proteins which are essential for the growth of the plants. Inhibition of the corresponding transporter protein should accordingly lead to impairment of growth. On the assumption that DNA sequences which code for the corresponding transporter protein are available, this detection is possible, for example, by means of expression or of antisense inhibition of the corresponding gene in transgenic plants (Willmitzer, Trends Genet. 4: 13–18, 1988). The techniques for producing such transgenic plants are known to a skilled person. Thus, for example, it has been possible to show, by expression of an antisense RNA which codes for the triose phosphate translocator, that even a small reduction in the expression of the protein leads to a drastic inhibition of growth of the plant (Riesmeier et al., Proc. Natl. Acad. Sci. USA 90: 6160–6164, 1993). It has likewise been possible to show for the sucrose transporter that a reduction in the activity leads to a great inhibition of growth of potato plants. Furthermore, the leaves of the affected plants are damaged, and the plants produce few or no potato tubers (Riesmeier et al., 1994, EMBO J. 13: 1–7). Since the formation or the organs of reproduction is greatly impaired, it can be expected that a suitable herbicide not only inhibits the growth of a plant but also impedes its reproduction. The same is to be expected in the case of ammonium and amino-acid transport because these have an essential function in metabolism for the transport of nitrogen.

On the basis of the described essential function, preferred embodiments of the present invention provide for the use of the transporter proteins for amino acids, sucrose and ammonium and as target proteins for finding potential active substances specific for plants, especially the use of the transporter proteins specified above.

Suitable genes coding for transporter proteins are introduced, with the aid of conventional methods of molecular genetics, into an organism or into cells in such a way that expression of a transporter protein capable of functioning is ensured.

The organism mentioned in step a) in the method is preferably a unicellular organism. The unicellular organism is chosen so that its cells can easily be cultivated and are suitable for expressing the transporter protein. Particularly suitable for this purpose are microorganisms such as bacteria, fungi or yeasts. However, it is also possible to use single cells of an organism. Also suitable for use in the method according to the invention are, for example, plant cells maintained in cell culture, or callus cultures, as well as animal cells in cell culture, especially including oocytes, preferably *Xenopus oocytes*. The transgenic cells obtained by introducing a plant transporter protein gene, or the recombinant organism obtained, can then as a whole be part of a test system or can be used to isolate membranes or purified transporter protein. The invention likewise relates to these recombinant organisms (bacteria, fungi and yeasts) and transgenic cells. A gene which codes for a transporter protein can additionally be introduced into a particular mutant of an organism which is unable to grow without the functioning of the corresponding transporter protein (Riesmeier et al., EMBO J. 11: 4705–4713, 1992). The use of such a mutant has the particular advantage that it makes it possible for growth of the recombinant organism in a suitable medium to serve as a measure of the functioning of the transporter, and thus to describe quantitatively the effect of the substances to be investigated on membrane transport. The growth test is distinguished by being particularly simple to operate and by rapid throughput of substances. It is therefore preferred to use suitable mutants as have been described, for example, for sucrose transporters (SUSY7; see Riesmeier et al., EMBO J. 11: 4705–4713, 1992), aminoacid transporters (yeast mutants 22574d and JT16; see Frommer et al., Proc. Natl. Acad. Sci. USA 90: 5944–5948, 1993; yeast mutant shr3; see Ljungdahl et al., 1992, Cell 71: 463–478) and ammonium transporters (Ninnemann et al., 1994, EMBO J. 13: 3464–3471).

The appropriate transporter gene is used according to the invention to transform said organism or cells.

The recombinant organism or the transgenic cells can then be multiplied as desired by conventional microbiological methods and are thus available to an unrestricted extent for use in the test system. A multistage procedure is preferred for testing substances for herbicidal and/or growth-regulating properties: firstly recombinant organisms or transgenic cells are cultured in a medium in which an essential growth substrate is chosen so that it enters the cells only through the transporter to be investigated and, in addition, cannot be functionally replaced by any other substrate in the medium. In the case of a sucrose transporter, for example, the medium contains sucrose as the sole carbon source, in the case of an amino-acid transporter the medium contains, for example, an amino acid which serves as sole carbon or nitrogen source for the cells, and in the case of an ammonium transporter the medium contains ammonium as sole nitrogen source. The substances to be investigated are added to the medium during the growth phase, and the growth of the cells is determined by conventional methods.

In order to detect a specific interaction of a substance with a membrane transporter, and in order to preclude other modes of action as cause of the inhibition of growth, the substance must meet the following conditions:
1) Recombinant cells must show distinctly less growth after addition of the substance than without addition of the substance.
2) The same organisms must not be inhibited in growth after addition of the substance if another growth substrate is present in the medium, is able functionally to replace the actual substrate of the transporter in the cells, and itself does not enter the cells via the corresponding transporter.

Yeast cells are able, for example, to grow either with sucrose or with an amino acid as carbon source. Yeasts are able to utilize either an amino acid or ammonium ions as nitrogen source.

If a substance meets the stated conditions, it can be further investigated in a biochemical test. This test measures the membrane passage of the natural substrate or of the inhibiting substance. It is possible to employ for this purpose whole yeast cells or isolated membrane vesicles. Membrane passage of the transporter substrate or of the inhibiting substance can be detected by the substrate or the substance being isolated from the cells or membrane vesicles which have been separated off, and being detected by conventional analytical methods. As a rule, the substrate or the substance will be added in radiolabeled form and subsequently analyzed via its radioactive emission. The type of inhibition can be determined by altering the concentrations of the substrate and of the inhibiting substance using conventional biochemical methods. It is furthermore possible to detect thereby whether the substance itself is transported by the transporter.

If a substance meets the abovementioned conditions, it can be investigated, with or without further biochemical investigations, directly on whole plants or suitable parts of plants for its herbicidal action or for its mobility in the plant. Conventional herbological and physiological methods can be used for this purpose.

The invention likewise relates to the substances which can be identified by the method according to the invention and which have a herbicidal and/or growth-regulating action on plants, and to the formulation thereof with other herbicides, growth regulators, nematicides, insecticides, acaricides, fungicides and auxiliaries conventional in agriculture.

The method according to the invention can also be used to identify substances which are themselves conveyed by the transporter protein (transporter) through the plant cell membrane. The invention likewise relates to these substances. The method can thus be used to identify those chemical structures which are transported particularly well in the plant. This property of good mobility is particular desired for crop protection agents such as herbicides and insecticides.

The method according to the invention can also be used as test system for identifying transportable chemical structures. Since sucrose and amino-acid transporters represent the main transport systems for organic molecules in the membranes, it is possible, for example, to utilize the yeast system as simple test for investigating the mobility of organic substances in the plant. The preferred procedure in this connection is multistage: it is possible in the first place to investigate the uptake of foreign substances in a growth test. It is then possible, building on this, to employ direct measurements of transport in intact yeasts or isolated membranes for more detailed investigation. Yeasts which do not contain the transporter are always available as control. Besides yeasts, it is also possible to use for this purpose other organisms, especially unicellular organisms, and especially cell cultures of animal or plant cells.

In the event of specific impairment of transport there should be observed to be a reduction in growth of the transgenic yeasts. It is possible by investigating the transporters to gain a better understanding of which properties of a substance are necessary for transport-ability. It would be possible for a number of substances which have hitherto been ineffective as pesticides because of a lack of transport-ability to alter the molecules chemically so that they acquire these properties of a substance and thus reach their site of action better. It would likewise be conceivable to alter the transporters by methods of molecular biology or by mutation in such a way that they are better able to transport the pesticides, such as insecticides and herbicides, through membranes. The altered transporter protein genes can then in turn be introduced into plants.

The present invention likewise relates to the use of such transporter proteins which transport pesticides through plant cell membranes.

The invention likewise relates to pesticides, especially herbicides and growth regulators, which are able to inhibit the plant transport system, where the plant transport system (transporter) is, for example, the sucrose, the ammonium or the amino-acid transporter.

Besides the finding of substances, the system can also be employed for investigating other important questions, eg. what are the structures of such proteins and how the substrates are recognized, or [sic] and in which connection the structure is related to the function, and how generally substances are distributed in an organism. The method which has led to isolation and characterization of the described transporters can, however, also be employed for isolation of other proteins (eg. ion transporters or transport proteins from animal systems) and for investigation in the same manner.

The following examples of use illustrate the subject-matter of the invention without restricting it. The use of plant sucrose, amino-acid and ammonium transporters for identifying substances which have inhibitory effects on these transporters is described.

EXAMPLES OF USE

Example 1

Identification of inhibitors of slant amino-acid transporters

Transporter investigations are carried out on the yeast mutant 22574d (Jauniaux & Grenson, Eur. J. Biochem. 190: 39–44, 1990), which harbors a mutation in the gene for amino-acid permease, and on the yeast mutant JT 16 (Tanaka and Fink, Gene 38: 205–214, 1985) which is incapable of histidine uptake, for identification of inhibitors of plant amino-acid transporters. These mutants are transformed with cDNA sequences which code for plant amino-acid transporters and lead to expression of functional transporters in the yeast cells. The cDNA sequences are cDNA sequences which code for the amino-acid transporters AAP1 and AAP2 from *Arabidopsis thaliana* (Frommer et al., 1993, Proc. Natl. Acad. Sci. USA 90: 5944–5948; Kwart et al., 1993, Plant J. 4:993–1002). For the measurements, cells of these mutants are cultured in minimal medium (NAAG+5 mmol/l proline) at 28° C. and harvested in the logarithmic phase ($OD_{600}$=0.6). The cells are spun down in a centrifuge at 4000 rpm and 4 degrees Celsius for 10 minutes and washed 2× with AUB buffer (modified AAB buffer, Ljungdahl et al.). The cell concentration is adjusted to an $OD_{600}$ of 25 in AUB buffer.

| Media and buffer used: | |
|---|---|
| NAAG medium: | 1.7 g/l yeast nitrogen base, w/o amino acids |
| and | ammonium sulfate |
| SDGlu medium: | 10 g/l glucose |
| | 20 g/l agarose |
| | 6.7 g/[lacuna] yeast nitrogen base w/o amino acids |
| SDsuc medium: | 20 g/l gucose [sic] |
| | 20 g/l agarose |
| | 6.7 g/[lacuna] yeast nitrogen base w/o amino acids |
| | 20 g/l sucrose |
| | 20 g/l agarose |
| AUB buffer: | 10 mmol/l MES |
| | 2 mmol/l magnesium chloride |
| | 0.6 mmol/l sorbitol |

100 μl portions of the cell suspension are mixed with 100 μl of a 1 mmol/l L-proline solution (18.5 kBq of L-[14C]-proline) and various concentrations of the appropriate substance to be investigated. After 20, 60, 120 and 180 seconds, a 50 μl aliquot is removed, diluted in 4 ml -of ice-cold AUB buffer and filtered through glass fever [sic] filter. In order to remove nonspecifically bound L-[14C]-proline, the cells are washed 2× with 4 ml of ice-cold water each time. The radioactivity retained on the glass filter is then measured in a liquid scintillation counter. The radioactivity reflects the amount of radiolabeled proline taken up by the cells. Uptake of radiolabeled proline without addition of a potential inhibitor is determined as one control. Cells of each of the mutants 22574d and JY 16 which have not been transformed with cDNA sequences coding for plant amino-acid transporters are used as further control. Results of measurements of this type on the mutants 22457d-AAP2 which expresses the amino-acid transporter AAP2 from *Arabisopsis* [sic] *thaliana* are shown in the following table.

| Tested substance | Concentration | Activity relative to control [%] |
|---|---|---|
| CCCP | 10 μM | 15.6 ± 2.1 |
| DNP | 0.1 mM | 7.6 ± 1.6 |
| DEPC | 1 mM | 3.1 ± 1.2 |
| Azetidine-2-carboxylate | 10 mM | 62 |
| D-Proline | 10 mM | 90 |

For the investigations, yeast cells of the strain 22457d were transformed with a cDNA sequence which codes for the amino-acid transporter AAP2, and the uptake of radio-labeled proline in the presence of various substances was determined. The various substances tested, their concentration, and the activity of the transporter, shown as percentage activity of the control with which no potential inhibitors were added, are indicated.

Substances which specifically show an inhibitory effect on the amino-acid transporter AAP2 are tested on whole plants for their herbicidal and growth-regulating effect.

Example 2

Identification of inhibitors of the sucrose transporter from *Spinacia oleracea*

Yeast cells of the strain SUSY7 (Riesmeier et al., 1992, EMBO J. 11: 4705–4713) are used to identify substances which have an inhibitory effect on sucrose transporters from spinach. Cells of this strain are transformed with a cDNA sequence which codes for the sucrose transporter S21 (SoSUT1) from spinach and which ensures expression of a functional transporter in the cells. The yeast cells are cultured in minimal medium (SD+2% (w/v) sucrose, pH 3.8) at 28° C. and harvested in the logarithmic phase ($OD_{600}$=0.6). The cells are spun down at 4000 rpm for 10 minutes and washed twice with SD medium. A cell concentration of c=50 g/l in SD medium is adjusted according to the wet weight of the cells, and 200 μl aliquot fractions are taken. Before the actual reaction, the cells are incubated in 10 mM glucose for 5 min and adjusted to pH 3.8 with MES buffer. The reaction is started by adding 200 μl of a 0.2 mmol/l [14C]-sucrose solution (3 mCi/mmol) in SD medium (pH 3.8). After 20, 60, 120, 180 and 240 seconds, 70 μl portions of the suspension are removed and pipetted into 4 ml of ice-cold water in order to stop the reaction. The cells are filtered off on glass fiber filters and washed twice with ice-cold water. The radioactivity on the filters is subsequently determined in a liquid scintillation counter. The substances to be tested are added 30 seconds before addition of the sucrose. The uptake of radiolabeled sucrose without addition of a potential inhibitor is determined as one control. Cells of the strain SUSY7 which are not transformed with cDNA sequences coding for a sucrose transporter from spinach are employed as further control. The results of transport measurements of this type are shown in the following table.

| Tested substances | Concentration | Activity relative to the control [%] |
|---|---|---|
| CCCP | 10 µM | 10 |
| PCMBS | 0.1 mM | 21 |
| DEPC | 0.5 mM | 6 |
| Palatinose | 2 mM | 85.0 |
| Mannose | 2 mM | 86.5 |
| Tagatose | 2 mM | 104.7 |
| Melizitose [sic] | 2 mM | 97.2 |
| Raffinose | 2 mM | 110.3 |
| Galactose | 2 mM | 97.7 |
| Cellobiose | 2 mM | 99.4 |
| Melibiose | 2 mM | 92.3 |
| Altrose | 2 mM | 80.6 |
| α-Lactose | 2 mM | 81.8 |
| β-Lactose | 2 mM | 94.9 |
| α-Phenylglucose | 2 mM | 8.0 |
| 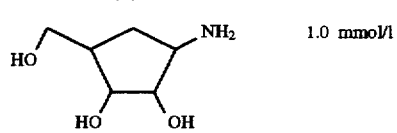 | 1.0 mmol/l | 0 |
| 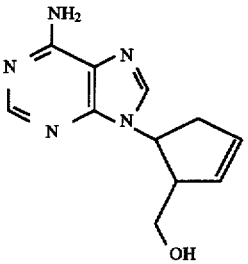 | 1.0 mmol/l | 0 |

The various tested substances, their concentration and the activity of the transporter, shown as percentage activity of the control in which no potential inhibitors were added, are indicated. Substances which specifically show an inhibitory effect on the sucrose transporter S21 (SoSUT1), are tested for their herbicidal and growth-regulating effect on whole plants. Some of the identified inhibitors of the sucrose transporter have herbicidal activity on plants, for example PCMBS.

Example 3
Identification of inhibitors of the sucrose transporter from *Solanum tuberosum*

Yeast cells of the strain SUSY7 (Riesmeier et al., 1992, EMBO J. 11: 4705–4713) are used to identify substances which have an inhibitory effect on sucrose transporters from potato. Cells of this strain are transformed with a cDNA sequence which codes for the sucrose transporter P62 (StSUT1) from potato (WO 94/00574, Riesmeier et al., 1993, Plant Cell 5:1591–1598) and which ensures expression of a functional transporter in the cells. The resulting yeast strain was called SUSY-7-P62 (StSUT1). The yeast cells are cultured in minimal medium (SD +2% (w/v) sucrose, pH 3.8) at 28° C. and harvested in the logarithmic phase ($OD_{600}$=0.6). The cells are spun down at 4000 rpm for 10 minutes and washed twice with SD medium. A cell concentration of c=50 g/l in SD medium is adjusted according to the wet weight of the cells, and 200 Al aliquot fractions are taken. Before the actual reaction, the cells are incubated in 10 mM glucose for 5 min and adjusted to pH 3.8 with MES buffer. The reaction is started by adding 200 Al of a 0.2 mmol/l [14C]-sucrose solution (3 mCi/mmol) in SD medium (pH 3.8). After 20, 60, 120, 180 and 240 seconds, 70 µl portions of the suspension are removed and pipetted into 4 ml of ice-cold water in order to stop the reaction. The cells are filtered off on glass fiber filters and washed twice with ice-cold water. The radioactivity on the filters is subsequently determined in a liquid scintillation counter. The substances to be tested are added 30 seconds before addition of the sucrose. The uptake of radiolabeled sucrose without addition of a potential inhibitor is determined as one control. Cells of the strain SUSY7 which are not transformed with cDNA sequences coding for a sucrose transporter from potato are employed as further control. The results of transport measurements of this type are shown in the following table.

| Tested substances | Concentration | Activity relative to the control [%] |
|---|---|---|
| CCCP | 10 µM | 9 |
| PCMBS | 0.1 mM | 20 |
| 2,4-DNP | 0.1 mM | 3 |
| DEPC | 0.5 mM | 6 |
| N-Ethylmaleimide | 1 mM | 22 |
| Palatinose | 2 mM | 102 |
| Tagatosa | 2 mM | 103 |
| Raffinose | 2 mM | 110 |
| β-Lactose | 2 mM | 91 |
| α-Phenylglucose | 2 mM | 7 |

The various tested substances, their concentration and the activity of the transporter, shown as percentage activity of the control in which no potential inhibitors were added, are indicated.

Substances which specifically show an inhibitory effect on the sucrose transporter P62 (StSUT1), are tested for their herbicidal and growth-regulating effect on whole plants. Some of the identified inhibitors of the sucrose transporter have herbicidal activity on plants, for example PCMBS.

Example 4
Determination of the substrate specificity of the sucrose transporter

The investigations of the substrate specificity and the $K_m$ determination are carried out in the yeast strain SUSY7-pP62 (StSUT1) (Riesmeier et al., 1993, Plant Cell 5:1591–1598), which expresses the sucrose transporter from Solanum tuberosum. This entails carrying out the method of Example 3 apart from the fact that the substrate concentration is changed and no potential inhibitors are added. To control for the background activity, the uptake of [14C]-sucrose by the yeast strain SUSY7 which does not express the transporter is determined. This strain shows no measurable uptake of [14C]-sucrose over the measurement period. Test results:

| $K_m$ for sucrose | 1 mM |
|---|---|
| $K_m$ for maltose | 10 mM |

Example 5
Activation of sucrose transport

The transport of sucrose by the sucrose transporter P62 (StSUT1) from *Solanum tuberosum* can be increased by previous energizing of the yeast cells by incubation in glucose, stachyose and adenine. The same increase in transport activity is achieved by reducing the pH to pH 3.8 in the measurement. The measurement of transport to determine the activation takes place as described in Example 3 but the cells are incubated before the actual measurement not in 10 mM glucose for 5 min but in solutions of various concentrations of glucose, stachyose and adenine for 5 min. Yeast cells which are not incubated in solutions of these substances before the measurement act as control. The following table indicates the extent of activation of sucrose transport with various concentrations of glucose, stachyose and adenine compared with the control.

|  | Activity relative to the control [%] | |
|---|---|---|
|  | c1 [0.2 mol/l] | c2 [2 mmol/l] |
| Glucose | 89 ± 5 | 90 ± 3 |
| Stachyose | 144 ± 9 | 101 ± 8 |
| Adenine | 141 ± 5 | 225 ± 6 |

Stachyose stimulates sucrose transport at low concentrations, while this effect is reversed at high concentrations (c>0.4 mmol/l), and stachyose begins to reduce the uptake. For adenine there is a linear relation between the adenine concentration and the increase in the sucrose transport rate. It can be shown by competition studies which domains are important for the affinity of the transporter for sucrose.

Example 6
Identification of inhibitors of Plant ammonium transporters

The measurements of transport identify inhibitors of plant ammonium transporters are carried out with the structural analog methylamine because radiolabeled ammonium is not commercially obtainable.

Yeasts of the yeast strain ∑ 26972c (Dubois & Grenson, Mol. Gen. Genet. 175: 67–76, 1979) which harbor mutations in the $NH_4^+$ permease genes MEP1 and MEP2 are used for the investigations.

The yeast cells are transformed by standard methods with cDNA sequences which code for an ammonium transporter from plants and which permit expression of a functional transporter in the yeast cells. This is the transporter AMT1 from Arabidopsis thaliana (Ninnemann et al., 1994, EMBO J. 13:3464–3471). The cells are cultured in NAAG-medium (2% glucose, 1.7 g/l yeast nitrogen-base w/o amino acids and ammonium sulfate (Difco), supplemented with 500 µg/ml L-proline) at 28 degrees Celsius, and harvested in the logarithmic phase ($OD_{660}$=0.6). The cells are then spun down in a centrifuge at 4000 rpm and 4 degrees Celsius for 10 minutes, washed twice with 20 mM sodium phosphate buffer, pH 7, and taken up in the same buffer to an $OD_{660}$ of 8. 200 µl aliquot fractions of the cell suspension are taken. 5 minutes before the actual measurement, the yeasts are activated by addition of 100 mM glucose and incubated at 30 degrees Celsius. To start the reaction, 100 µl of the cell suspension are added to 100 l of reaction mixture (20 mM Na phosphate buffer, pH7; 18.5 kBq of [$^{14}C$]-methylamine (NEN); 100 M methylamine; substance to be tested depending on the experiment (see FIG. 4)). In each case 10, 60, 120 and 180 seconds after starting the reaction, 50 µl aliquots are taken, added to 4 ml of ice-cold 5 mM methylamine solution and filtered on glass fibre filters. After the filters have been washed with a further 8 ml of a methylamine solution, the radioactivity on the filters is subsequently determined in a liquid scintillation counter. Inhibitors are added 60 seconds before adding the glucose.

The uptake of radiolabeled methylamine without addition of a potential inhibitor is determined as one control. The same transport investigations are carried out on yeast cells of the strain ∑26972c which have not been transformed as further control.

The results of investigations of this type are shown in the following table.

| Tested substances | Concentration | Activity relative to the control [%] |
|---|---|---|
| None | / | 100 |
| Methylamine | 500 µM | 40 |
| Dimethylamine | 500 µM | 89 |
| Trimethylamine | 500 µM | 89 |
| Ethylamine | 500 µM | 93 |
| KCl | 500 µM | 98 |
| RbCl | 500 µM | 96 |
| CsCl | 500 µM | 98 |
| $NH_4Cl$ | 500 µM | 10 |
| Cycloheximide | 10 µg/ml | 85 |
| Antimycin A | 10 µg/ml | 8 |
| DCCD | 200 µM | 15 |
| 2-4 DNP [sic] | 100 µM | 18 |
| CCCP | 10 µM | 40 |

The various tested substances, their concentration and the activity of the transporter, shown as percentage activity of the control in which no potential inhibitors were added, are indicated.

Substances which specifically show an inhibitory effect on the ammonium transporter AMT1, are tested for their herbicidal and group-regulating effect on whole plants.

Some of the identified inhibitors of the ammonium transporter have herbicidal activity on plants, for example methylamine.

Example 7
Determination of the substrate specificity of the ammonium transporter AMT1 from Arabidopsis thaliana The investigations of the substrate specificity and the $K_m$ determinations are carried out with the yeast strain ∑ 26972c (Dubois & Grenson, Mol. Gen. Genet. 175: 67–76, 1979) which expresses the plant ammonium transporter AMT1. The method for this is as in Example 6, except for the fact that the methylamine substrate concentration is varied. To control for the background activity, the uptake of [$^{14}C$]-methylamine by a yeast strain which does not express said transporter is determined. To determine the affinity of the transport system for ammonium, the inhibition of methylamine transport by various concentration [sic] of ammonium is determined (inhibitor constant, $K_i$)

| $K_m$ for methylamine | 65 µM |
|---|---|
| $K_i$ for ammonium | <10 µM |

We claim:
1. A method for identifying substances which have a potential herbicidal or growth-regulating action which arises due to inhibition or inactivation of a plant transport process, which comprises.
   a) initially preparing a transporter protein by heterologous expression of a DNA sequence which codes for said transporter protein in a transgenic plant fungus, yeast or eukaryotic cell, subsequently b) employing said transgenic plant, fungus, yeast or eukaryotic cell for assaying a chemical compound for its inhibitory effect on said transporter protein, and c) additionally assaying the chemical compound for activity on plant, fungus, yeast or eukaryotic cell which do not produce the corresponding transporter protein, in order to preclude the possibility that the chemical compound also has an inhibitory effect on other mechanisms in said plant, fungus, yeast or eukaryotic cell, and finally d) testing the chemical compound which is active against the transporter protein for its herbicidal or growth-regulating activity on plants.

2. A method as claimed in claim 1, wherein the transporter is a sucrose transporter.

3. A method as claimed in claim 1, wherein the transporter is an amino-acid transporter.

4. A method as claimed in claim 1, wherein the transporter is an ammonium transporter.

5. A method as claimed in claim 1, wherein the organism is a fungus or yeast.

6. A method as claimed in claim 1, wherein the cells are plant cells.

7. A method as claimed in claim 1, wherein the cells are animal cells.

8. A method as claimed in claim 1, wherein the cells are oocytes.

9. A method as claimed in claim 1, wherein the cells are Xenopus oocytes.

* * * * *

UNITED STATES PATENT AND TRADEMARK OFFICE
CERTIFICATE OF CORRECTION

PATENT NO.: 5,750,362

DATED: May 12, 1998

INVENTOR(S): FROMMER et al.

It is certified that error appears in the above-identified patent and that said Letters Patent is hereby corrected as shown below:

Col. 12, claim 1, line 65, "." should be --:--.

Col. 13, claim 1, line 1, after "plant" insert --,--.

Signed and Sealed this

Sixth Day of October, 1998

*Attest:*

BRUCE LEHMAN

*Attesting Officer*     *Commissioner of Patents and Trademarks*